US007795204B2

(12) United States Patent
Gardiner et al.

(10) Patent No.: US 7,795,204 B2
(45) Date of Patent: *Sep. 14, 2010

(54) FOOD SUPPLEMENT FOR INCREASING LEAN MASS AND STRENGTH

(75) Inventors: Paul T. Gardiner, Mississauga (CA); Derek E. Woodgate, Guelph (CA); Mark S. Gilbert, Staffordshire (GB); Robert W. Thoburn, Costa Mesa, CA (US)

(73) Assignee: Northern Innovations and Formulations Corp., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/799,038

(22) Filed: Mar. 11, 2004

(65) Prior Publication Data

US 2004/0175443 A1 Sep. 9, 2004

Related U.S. Application Data

(60) Division of application No. 09/482,688, filed on Jan. 13, 2000, now Pat. No. 6,784,209, which is a continuation-in-part of application No. 09/420,439, filed on Oct. 18, 1999, now abandoned.

(51) Int. Cl.
*A61K 9/14* (2006.01)
*A61K 31/195* (2006.01)
*A61K 31/205* (2006.01)
*A61K 31/519* (2006.01)
*A61K 31/70* (2006.01)
*A61K 31/715* (2006.01)
*A61K 36/258* (2006.01)
*A61K 38/00* (2006.01)
*A61P 3/02* (2006.01)

(52) U.S. Cl. .................. 514/2; 424/489; 424/499; 424/728; 514/23; 514/54; 514/262.1; 514/556; 514/561; 514/562; 514/564; 514/565

(58) Field of Classification Search .......... 514/2, 514/23, 54, 562, 563, 564, 565, 566, 567, 514/568, 569, 570, 578, 665, 729, 738; 424/725, 424/728; 426/648, 656, 658
See application file for complete search history.

(56) References Cited

U.S. PATENT DOCUMENTS

| 4,710,387 | A | | 12/1987 | Uiterwaal et al. |
| 5,124,360 | A | | 6/1992 | Larner et al. |
| 5,324,656 | A | | 6/1994 | Ham et al. |
| 5,550,166 | A | * | 8/1996 | Ostlund et al. ............. 514/715 |
| 5,744,157 | A | | 4/1998 | Droge |
| 5,817,329 | A | | 10/1998 | Gardiner |
| 5,891,441 | A | | 4/1999 | Diaz et al. |
| 5,902,829 | A | | 5/1999 | Schneider et al. |
| 6,004,926 | A | * | 12/1999 | Shimizu et al. ................. 514/2 |
| 6,019,999 | A | * | 2/2000 | Miller et al. ................. 424/450 |
| 6,051,236 | A | | 4/2000 | Portman |
| 6,117,872 | A | | 9/2000 | Maxwell et al. |
| 6,482,448 | B2 | * | 11/2002 | Tabor ........................ 424/757 |
| 6,784,209 | B1 | * | 8/2004 | Gardiner et al. ............. 514/565 |
| 2001/0041187 | A1 | * | 11/2001 | Hastings et al. ............. 424/439 |

FOREIGN PATENT DOCUMENTS

| CN | 1201599 | 12/1998 |
| JP | 60054321 | 3/1985 |
| JP | 63109736 | 5/1988 |
| JP | 63310827 | 12/1988 |

OTHER PUBLICATIONS

PUBMED online, file MEDLINE, PMID 761710 (Goldberg, Diabetes (1979), vol. 28, Supp. 1, pp. 18-24), Abstract.*
PUBMED online, file MEDLINE, PMID 128681 (Goldberg et al., Med. Sci. Sports (1975), vol. 7, No. 3, pp. 185-198), Abstract.*
Goldsmith et al., Treatment of soy whey by membrane processes [Retrieved on Oct. 20, 2008], Retrieved from the Internet: <URL:http://www.p2pays.org/ref/19/18681.pdf>.*
STN online, file CAPLUS, Acc. No. 1997:529398, Doc. No. 127:204709 (Bae et al., Isoflavone contents and antioxidant effects of soybeans, soybean curd and their byproducts, Han'Guk Sikp'um Yongyang Kwahak Hoechi (1997), vol. 26, No. 3, pp. 371-375), Abstract.*
Burke, D.G., et al. The effect of whey protein supplementation and resistance training on body composition and strength. Med Sci Sports Exer. 32 (5): s330, May 2000.
Kalman, D.S. et al. A clinical evaluation of the safety of high protein intake over 28 days in healthy resistence trained men ACSM, 2001.
Swain, M. et al. Effects if whey protein concentrate/isolate supplementation versus whey protein concentrate in weight-trained athletes: A double blind trial. American College of Nutrition conference, Oct. 12-15, Oct. 2000.
Haglind, C. et al., Effects of caffeine containint energy drinks, International Food Information Service (IFIS) Frankfurt/Main, Germany & Scandinavian Journal of Nutrition 43 (4) 169-175 1999 Sports Club, Stavgrand 16, 129 48 Hagersten, Sweden. Abstract.
Beltz, Susan Durden et al., Efficacy of nutritional supplements used by athletes, Biosciences Information Service, Philadelphia, Pennsylvania, 1993; & Clinical Pharmacy, vol. 12, No. 12, 1993, pp. 900-908. Abstract.
Williams, Melvin H., Nutritional ergogenics in athletics. Biosciences Information Service, Philadelphia, Pennsylvania, 1995; & Journal of Sports Sciences, vol. 13. No. Spec. Issue 1995, pp. S63-S74. Abstract.

(Continued)

*Primary Examiner*—Johann R Richter
*Assistant Examiner*—Frank I Choi
(74) *Attorney, Agent, or Firm*—Fitzpatrick, Cella, Harper & Scinto

(57) ABSTRACT

Food supplement compositions and their methods of use in increasing lean mass and/or muscle size and/or strength in individuals, particularly, athletes is described. The food supplements described comprise a substance which increases nitric oxide production in the body, and, a source of amino acids. Other food supplements described comprise a substance which can enhance and/or mimic insulin activity, and a source of amino acids. The food supplement compositions described are suitable for supplementing the diet of an athlete and particularly for enhancing an athlete's muscle size or strength.

16 Claims, No Drawings

OTHER PUBLICATIONS

Jablecki et al., '[3H] inositol incorporation into phosphatidyl-inositol in work-induced growth of rat muscle,' Am. J. Phisiol. (1977), 232(3), pp. E324-E329).

Doi et al., Int. Congr. Ser.—Excerpta Med. (1982), 549 (Genet. Environ. Interact Diabetes Millitus), pp. 306-312.

Kim et al., 'Ginsenosides protect pulmonary vascular endothelium against free radical-induced injury,' Biochem. Biophys, Res. Commun. (1992), 189(2), pp. 670-676.

Kolla et al., Izuch, Biol. Deistivya Prod. Org. Sint. Prir. Soedin (1976), pp. 116-121.

"FDA displays premarket notifications for new ingredients, pinitol and DHA-rich oil," Food Chemical News (1998), vol. 40, No. 7.

Campbell et al., 2004, Pinitol Supplementation Does Not Affect Insulin-Mediated Glucose Metabolism and Muscle Insulin Receptor Content and Phosphorylation in Older Humans Amer. Society for Nutritional Sciences, 2998-3003.

Davis et al., 2000, "Effect of Pinitol Treatment on Insulin Action in Subjects with Insulin Resistance", Diabetes Care, 23(7):1000-1005.

Urbano et al., 2000, "The role of phytic acid in legumes: antinutrient or beneficial function?", J. Physiol. Biochem., 56(3): 283-294.

Waagbø et al., 1998, "Effects of inositol supplementation on growth, chemical composition and blood chemistry in Atlantic salmon, *Salmo salar* L., fry", Aquaculture Nutrition, 4: 53-59.

Burke, et al., "The Effect of Whey Protein Supplementation With and Without Creatine Monohydrate Combined With Resistance Training on Lean Tissue Mass and Muscle Strength", International Journal of Sport Nutrition and Exercise Metabolism, vol. 11 (2001) 349-64.

Lu, et al., "Liposomal Dry Powders as Aerosols for Pulmonary Delivery of Proteins", AAPS PharmSciTech, vol. 6, No. 4 (2005) E641-48.

Antonione, et al., "Whey Protein Ingestion Enhances Postprandial Anabolism during Short-Term Bed Rest in Young Men", The Journal of Nutrition, vol. 138 (2008) 2212-16.

\* cited by examiner

FOOD SUPPLEMENT FOR INCREASING LEAN MASS AND STRENGTH

CROSS-REFERENCE TO RELATED APPLICATIONS

This application is a divisional of U.S. patent application Ser. No. 09/482,688 filed Jan. 13, 2000 now U.S. Pat. No. 6,784,209, which is a continuation-in-part of patent application Ser. No. 09/420,439 (now abandoned) filed on Oct. 18, 1999, each of which is expressly incorporated herein by reference in its entirety.

FIELD OF INVENTION

The present invention is directed to food supplements which comprise nitric oxide or derivatives thereof, and a source of amino acids or derivatives thereof; supplements which stimulate nitric oxide in the body, and a source of amino acids; supplements which enhance and mimic insulin activity; and to methods for supplementing the diet of an athlete and methods for enhancing an athlete's muscle size and/or strength, which methods employ these food supplements.

BACKGROUND OF INVENTION

Food supplements for enhancing an athlete's muscle size and strength have become popular substitutes for steroids and other drugs in various sports and body building regimes. However, as athletes continually strive for improved performance, there is a continuing need for non-steroid containing aids for increasing lean mass, muscle size and strength.

SUMMARY OF THE INVENTION

Nitric oxide plays an essential role in tonic and exercise-associated (e.g., recovery from exercise) regulation of vasodilation and blood flow. The present inventor has found that increased NO through supplementing the diet of an athlete with substances which increase the concentration of nitric oxide (NO) or increase its half life in the body, in combination with a source of amino acids, may provide surprising enhancement of an athlete's muscle size or strength when administered to an athlete's diet. Accordingly, in one broad aspect the present invention provides new food supplements to increase the delivery and duration of nitric oxide in the body. These food supplements do not themselves contain nitric oxide; rather, they act to promote the production of nitric oxide or to enhance its half life in the body. Preferably the invention provides food supplements particularly adapted for supplementing the diet of an athlete, preferably the food supplements of the present invention enhance an athlete's muscle size and/or strength.

According to one embodiment of the present invention there is provided a food supplement comprising a substance which increases nitric oxide production in the body, and, a source of amino acids.

Preferably the substance which increases nitric oxide production may act by stimulating insulin levels in the circulation, and, a source of amino acids.

According to another preferred embodiment, the supplements of the present invention include a substance which may increase insulin sensitivity, and, a source of amino acids.

According to yet another aspect of the present invention, there is provided a supplement which may increase nitric oxide and thereby increase nitrogen retention in the body.

Preferably the supplement comprises a substance which may increase nitrogen retention in the body, in combination with a source of amino acids.

In another aspect, the present invention provides a food supplement comprising a substance which enhances and mimics insulin activity, and, a source of amino acids.

In another broad aspect, the present invention provides methods of supplementing bodybuilding in an athlete comprising administering to the athlete an effective amount of a food supplement according to the present invention to achieve an increase in muscle size and strength. Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The food supplements and methods of the present invention may provide further and significant muscle size and strength enhancement or improvement in individuals as compared with supplements and methods employing only proteins and/or amino acids. While it is expected that the supplements and methods of the present invention will be of importance to bodybuilders and other athletes, the supplements and methods of the invention are not limited to those groups. Rather, any individual may use the supplements and methods of the invention. Indeed, the supplements and methods may have applications to all animals.

Although the present invention is not to be limited by any theoretical explanation, it is believed that nitric oxide plays an essential role in tonic and exercise-associated (e.g., recovery from exercise) regulation of vasodilation and blood flow. Increased NO supports improved perfusion of skeletal muscle, which it is believed thereby stimulates oxidative metabolism, ATP and creatine phosphate biosynthesis, nutrient (e.g., amino acid) delivery and utilization for muscle (e.g., myofibrillar) protein synthesis, glucose delivery and uptake, glycogen synthesis, creatine delivery and uptake, creatine phosphate synthesis, fat loss regulation of nutrient-mediated insulin secretion, and nitrogen retention. The supplements according to the present invention are preferably based on a unique whey-protein system fortified with additional amino acids to further enhance the rapid absorption (i.e., of (-amino nitrogen) characteristics of whey which lend to its potent protein anabolic effects. Thus, combined with the metabolic effects of increased NO function, the supplements of the present invention effectively enhance the muscle protein anabolic effects of a source of amino acids, preferably any source of protein, more preferably whey.

The food supplements and methods of the present invention may provide further and significant size and strength enhancement through the role of certain substances which mimic and/or increase the sensitivity of insulin, in conjunction with a source of amino acid. Although the present invention is not to be limited by any theoretical explanation, it is believed that the family of substances known as the inositols, are physiological precursors to membrane protein anchors known as glycophosphatidylinositols (GPI). As used herein, "inositols" includes myo-inositol, cis-inositol, epi-inositol, allo-inositol, muco-inositol, neo-inositol, scyllo-inositol, d-chiro-inositol, 1-chiro-inositol, d-pinitol and myo-inositol. Hydrolysis of GPI releases in inositolphosphoglycans which are water soluble mediators of insulin signalling events. Accordingly, increased availability of these GPI precursors, increase insulin sensitive and these GPIs can trigger insulin signalling pathways and events independent of insulin thereby mimicking the effects of insulin. The pathways and events which are mimicked include, but are not limited to amino acid transport, protein synthesis, gene transcription, mRNA translation initiation, glucose uptake, glycogen storage, steroid hormones synthesis, and can thereby increase the development of muscle cells. Consequently, supplements which comprise a substance which can enhance and/or mimic insulin activity, and a source of amino acids, preferably any source of protein, more preferably, whey, may provide further and significant muscle size and strength enhancement as compared with supplements employing only proteins or amino acids.

The food supplements described herein comprise the compounds specifically identified and any derivatives thereof, for example a salt or ester. Suitable salts include, but are not limited to, alkali and alkaline earth metal salts, for example sodium, potassium or calcium salts, while suitable esters include, but are not limited to, alkyl esters, for example, methyl, ethyl or propyl esters, or lactone esters.

As used herein "source of amino acid" means any peptide, polypeptides, protein or any composition of individual amino acids or individual amino acid. Throughout the present specification, as a part of the food supplement of the invention whey protein or a derivative thereof are identified as the preferred source of amino acids or protein. Commercially available whey protein derivatives include WPI 97, Whey Peptides, WPC 80, and ION EXCHANGE whey protein. However, as will be readily appreciated by those skilled in the art, other sources of protein include milk protein, casein, any of the albumins including chicken egg albumin, and soy, may be used as a source of amino acids.

Supplements

According to one embodiment of the present invention there is provided a food supplement comprising a substance which increases nitric oxide production in the body in combination with a source of amino acids. As used herein, "a food supplement comprising a substance . . . in combination with a source of amino acids means the supplement contains both the substance which has an action as well as a source of amino acids. According to one aspect, an increase in nitric oxide production may be brought about by a substance selected from the group consisting of glycosidal saponins, ginseng, l-arginine, folic acid, bioflavonoids, for example, grape seed extract, and herbs, preferably l-arginine, most preferably ginseng.

According to one aspect of the present invention a substance which increases nitric oxide production may act by stimulating insulin levels in the circulation, preferably, the substance is selected from the group consisting of L-arginine, glycosidal saponins, for example, ginseng, and N-acetyl cysteine, most preferably ginseng.

According to another embodiment of the present invention, there is provided a food supplement comprising a substance which mimics and/or enhances insulin activity, the supplement also containing a source of amino acids. According to a preferred embodiment, a substance which mimics and/or enhances insulin activity is preferably selected from the group consisting of N-acetyl cysteine, myo-inositol, preferably d-myo-inositol, cis-inositol, epi-inositol, allo-inositol, muco-inositol, neo-inositol, scyllo-inositol, d-chiro-inositol, l-chiro-inositol, d-pinitol and glucomannan, most preferably glucomannan.

A source of amino acids is preferably selected from the group consisting of WPI 97, Whey Peptides, WPC 80, ION EXCHANGE, lactoferrin, whey protein, most preferably whey protein, although as indicated above, any other protein source may be used.

According to yet another aspect of the present invention, there is provided a supplement which may increase nitric oxide thereby increasing nitrogen retention in the body. Preferably the supplement comprises a substance which may increase nitrogen retention in the body, in combination with a source of amino acids. Preferably the substance which may increase nitrogen retention in the body is selected from the group consisting of glucomannan, glycosidal saponins, for example, ginseng, l-arginine, glutamine, methionine and leucine, preferably glucomannan, most preferably ginseng. The source of amino acids is preferably selected from the group consisting of WPI 97, Whey Peptides, WPC 80, ION EXCHANGE, lactoferrin, whey protein, most preferably whey protein.

As will be readily appreciated by those skilled in the art, the supplement is not limited to only one substance which by itself may increase nitric oxide, insulin output, insulin secretion, insulin sensitivity, and one source of amino acids. Indeed the present invention provides for combinations of substances and sources of amino acids, in differing amounts.

The food supplement compositions of the present invention may be provided in a variety of formats, for example, in liquid form, powder form, or protein bar form. Powders are preferable and are prepared to be suitable for mixing with water or other liquids. The food supplement compositions in powder or granular form may be provided in accordance with customary processing techniques, for example as spray dried powders, or the like.

According to one embodiment, the food supplement compositions of the present invention are delivered in powder on a per one "scoop" basis. As used herein, one "scoop" is approximately 28 g of supplement. According to one embodiment, one "scoop" comprises: glycosidal saponins (such as ginseng) from 1 mg-3000 mg; myo-inositol, from 1 mg-2000 mg; d-chiro-inositol, from 1 mg-2000 mg; and glucomannan, from 10 mg-4000 mg; and a source of amino acids, preferably protein, most preferably whey.

According to another embodiment a food supplement composition comprises, when delivered in powder form per one "scoop": glycosidal saponins, about 150 mg to about 1500 mg; myo-inositol about 100 mg to about 2000 mg; and glucomannan from about 25 mg to about 2000 mg; and a source of amino acids, preferably protein, most preferably whey.

According to another embodiment the food supplement composition comprises, when delivered in powder form per one "scoop": glycosidal saponins from about 50 mg to about 500 mg; glucomannan from about 50 mg to about 1000 mg; and myo-inositol, from about 200 mg to about 1000 mg, and a source of amino acids preferably protein, most preferably whey.

According to another embodiment, the food supplement composition comprises, when delivered in powder form per one "scoop": glucomannan from about 100 mg to about 500 mg; and a source of amino acids, preferably protein, most preferably whey.

According to yet another embodiment, the food supplement composition comprises, when delivered in powder form per one "scoop" glycosidal saponins at about 50 mg; and a source of amino acids, preferably protein, most preferably whey.

The food supplement compositions according to the present invention may further contain additional components to further increase the speed and or ease with which the substances enter the bloodstream and subsequently possibly impact the muscle tissue, or to otherwise enhance the effects of nitric oxide in the body. For example, additional amino acids may be included in the food supplement compositions. Suitable amino acids include, but are not limited to, glutamine, alanine, taurine, carnitine, acetyl-L-carnitine, and the like. These additional amino acids may stimulate cell volumization and protein synthesis and therefore provide further advantages to increasing muscle strength and/or size. These amino acids may be employed individually or in various combinations and in amounts customary in the art, for example in the range of from about 0.01 mg to about 1000 mg per gram of food supplement depending upon the amount of protein, or peptides, derived from whey or other source of amino acid in the supplement.

The food supplement compositions can also contain ascorbic acid (vitamin C), for example in amounts equal to or exceeding the recommended minimum daily requirements. Another component for possible use in the food supplements of the present invention comprises beta-hydroxy, beta-methyl butyrate (HMB), in amounts known in the art.

The food supplement compositions may further comprise natural and/or artificial flavouring components, dyes or other colouring additives, preservatives and other conventional food supplement additives known in the art.

Methods of Use of Supplements

The food supplements according to the present invention may be employed in methods for supplementing the diet of an athlete, and/or for enhancing an athlete's muscle size or strength. The food supplement compositions of the present invention are particularly advantageous for creating an increased anabolic environment and obtaining extra growth in lean muscle mass and strength. Accordingly, the present invention provides methods of supplementing bodybuilding in an athlete comprising administering to the athlete an effective amount of a food supplement according to the present invention. Administration of an "effective amount" of the supplements and substances of the present invention is defined as an amount effective, at dosages and for periods of time necessary to achieve the desired result. The effective amount of the supplements of the invention may vary according to factors such as the age, sex, and weight of the athlete. Dosage regima may be adjusted to provide the optimum response: Several divided doses may be administered daily or the dose may be proportionally reduced as indicated by the exigencies of the individual athlete situation.

As just stated, the amount of the food supplement composition which is administered to the diet of the athlete may vary depending on the desired effect, the body weight and characteristics of the athlete, and the like. For example, in preferred methods for supplementing the diet of an athlete and/or for enhancing an athlete's muscle size or strength, from about 0.5 to about 10 scoops of a supplement according to present invention are administered to the diet of the athlete on a daily basis.

In more preferred embodiments of these methods, from about 1 to about 6 scoops of a supplement according to the present invention are administered to the diet of the athlete on a daily basis. Number of scoops and frequency per day will depending upon the composition of the scoop, as outlined in variations set out above.

As will be readily appreciated a food supplement in accordance with the present invention may be administered in a single serving or in multiple servings spaced throughout the day. In a preferred embodiment, a food supplement in accordance with the present invention may be administered once in the morning, once immediately or shortly after training and once in the evening on a daily basis.

In order to maximize the effects of a food supplement according to the present invention, in enhancing muscle size and/or strength, it is preferred that the food supplement is administered to the diet of the athlete immediately following an exercise period. On non-workout days, the food supplement may be administered anytime during the day, although administering a first amount of a food supplement upon awakening or otherwise during the morning hours is preferred.

The food supplement compositions and methods of the invention are further illustrated in the following non-limiting examples. In the examples and throughout the present specification, parts and percentages are by weight unless otherwise specified.

EXAMPLES

Example 1

A muscle size and/or strength enhancing regime is initiated and established so that the athlete consumes three servings of the following food supplement daily, with each serving being 1 scoop which is approximately 28 g of the supplement and comprising:

| Per 1 scoop: | |
|---|---|
| Protein | 20 g |
| Carbohydrates | 3 g |
| Fiber | 1 g |
| Sugar | 2 g |
| Fat: | 1.5 g |

| INGREDIENT | AMOUNT/SERVING |
|---|---|
| SynthePro ™ A blend of the following constituting<br>WPI 97<br>WHEY PEPTIDES<br>WPC 80<br>ION EXCHANGE WHEY<br>LACTOFERRIN | 18 g |
| Nitroxen ™ A blend of the following constituting<br>ARGININE<br>GLYCOSIDAL SAPONINS<br>FOLIC ACID | 400 mcg |
| Insulogen ™ A blend of the following constituting<br>MYO-INOSITOL,<br>CIS-INOSITOL<br>EPI-INOSITOL<br>ALLO-INOSITOL<br>MUCO-INOSITOL<br>NEO-INOSITOL<br>SCYLLO-INOSITOL<br>D-CHIRO-INOSITOL<br>L-CHIRO-INOSITOL<br>INZITOL( (D-PINITOL)<br>GLUCOMANNAN | 200 mg |
| TAURINE | 100 mg |
| LEUCINE | |
| POTASSIUM PHOSPHATE | 100 mg |
| VIT E | 30 IU |
| NAC | 25 mg |

-continued

| | |
|---|---|
| VIT B6 | 10.5 mg |
| MAGNESIUM | 50 mg |
| The rest of the volume comprising the following: | |
| GUAR GUM | |
| METHIONINE | |
| GLUTAMINE PEPTIDES | |
| GLUTAMINE | |
| ALPHA-KETO GLUTARATE | |
| PHENYLALANINE | |

Each supplement serving is mixed with 6 ounces of cold water and the servings are administered approximately evenly spaced through the day, with a first serving in the morning, shortly after awakening, a second serving being consumed immediately after the athlete's exercise workout, and a third at a convenient time in the evening.

Example 2

A muscle size and/or strength enhancing regime as outlined in Example 1 is established so that the athlete consumes three servings of the food supplement daily, with each serving being 2 scoops which is approximately 56 g of the supplement.

Example 3

Where the regime in Example 1 or 2 is established, the athlete continues this regime on a day-to-day basis. As in Example 1 or 2, the serving is mixed with cold water to form a liquid drink. Alternatively, the food supplements may be combined with other liquid drinks or foods as desired. This regime is intended to last for the full term durng which an athlete is working out. The servings and their timing should also be consumed on non-workout days (with the second serving being taken mid-day) in order to maintain enhanced muscle size and/or strength.

The servings set forth in these examples are designed for a 2000 calorie diet. Daily values may be increased or decreased depending on the calorie needs of individual athletes, and/or body weights of individual athletes.

Example 4

Thirty-six experienced weight trained males were randomly assigned (double-blind) to one of three experimental groups: 1. a dietary supplement of a whey protein blend, comprising whey protein isolate 97%, creatine, glycosidal saponins, arginine, and glucomannan (WI)-1.2 g/kg/d whey protein, and 0.1 g/kg/d creatine; pure whey protein (W)-1.2 g/kg/d; or a placebo (P)-1.2 g/kg/d maltodextrin. Pre and post test measures consisted of 1-RM bench press, 1-RM squat, Biodex isokinetic leg extension power (ILP), and body composition as assessed by dual energy x-ray absorptiometry (DEXA). Training involved a 4-day split routine of high volume, heavy load periodized workouts with sets and reps varying from 4-5 sets and 4-10 reps. Each group experienced a significant change from baseline measure (p<0.05). Post hoc analysis revealed that the WI group demonstrated greated increases in lean muscle mass (+4.0 kg), 1-RM bench press (+16 kg), and ILP (+23 J/s) than W and P (p<0.05). The W group had a significantly greater increase in lean mass (+2.3 kg) and ILP (+18 J/s) than the P group (p<0.05). These findings indicate that whey protein supplementation when combined with resistance training for 6-weeks results in significant gains in muscular power and lean muscle mass, and when the whey protein is combined with other potentially ergogenic acids, even larger gains in muscle mass, 1-RM strength, and power occur.

The examples and embodiments set forth in the present application are provided only to illustrate various aspects of the invention and additional embodiments and advantages of the food supplements and methods of the present invention will be apparent to those skilled in the art.

We claim:

1. A method for supplementing the diet of a human to enhance muscle size and strength, comprising orally administering a dietary supplement, said dietary supplement comprising admixed effective amounts of:
   a powdered or granular protein selected from the group consisting of milk whey protein and milk whey peptides,
   at least one amino acid selected from the group consisting of glutamine, alanine, taurine, carnitine and acetyl-L-carnitine;
   a compound which is selected from the group consisting of myo-inositol, d-myo-inositol, cis-inositol, epi-inositol, allo-inositol, muco-inositol, neo-inositol, scyllo-inositol, d-chiro-inositol, 1-chiro-inositol and d-pinitol, and
   at least one ingredient which is selected from the group consisting of ginseng, L-arginine, N-acetyl cysteine, glucomannan and folic acid.

2. The method of claim 1, wherein the dietary supplement further comprises alpha-keto glutarate or guar gum.

3. The method of claim 1, wherein the dietary supplement further comprises alpha-keto glutarate and guar gum.

4. The method of claim 1, 2 or 3, wherein one serving of the supplement is about 28 grams and the supplement is administered more than once daily.

5. The method of claim 1, 2 or 3, wherein one serving of the supplement provides about 20 grams of protein and about 3 grams of carbohydrates.

6. The method of claim 1, 2 or 3, wherein one serving of the supplement further provides about 1.5 grams of fat.

7. The method of claim 1, 2 or 3, wherein the supplement is a powder.

8. The method of claim 7, wherein the powder is mixed with a liquid to provide a drink.

9. The method of claim 1, 2 or 3, which comprises taurine.

10. The method of claim 1, 2 or 3, wherein the dietary supplement is administered immediately after an exercise period.

11. The method of claim 1, 2 or 3, wherein one serving of the supplement provides about 20 grams of protein, about 3 grams of carbohydrates and about 1.5 grams of fat.

12. The method of claim 11, which comprises taurine.

13. The method of claim 12, wherein the dietary supplement is administered immediately after an exercise period.

14. The method of claim 11, wherein the dietary supplement is administered immediately after an exercise period.

15. The method of claim 1, 2 or 3, wherein said supplement is in the form of a bar.

16. The method of claim 1, 2 or 3, wherein said milk whey protein or milk whey peptides are granular.

* * * * *